(12) United States Patent
Carati et al.

(10) Patent No.: US 7,164,052 B2
(45) Date of Patent: Jan. 16, 2007

(54) CATALYTIC COMPOSITION FOR THE AROMATIZATION OF HYDROCARBONS

(75) Inventors: Angela Carati, Milan (IT); Marco Tagliabue, Milan (IT); Carlo Perego, Milan (IT); Roberto Millini, Milan (IT); Stefano Amarilli, Milan (IT); Giuseppe Terzoni, Piacenza (IT)

(73) Assignees: ENI S.p.A., Rome (IT); Enichem S.p.A., San Donato Milanese (IT); Enitecnologie S.p.A., San Donato Milanese (IT)

( * ) Notice: Subject to any disclaimer, the term of this patent is extended or adjusted under 35 U.S.C. 154(b) by 94 days.

(21) Appl. No.: 10/777,229

(22) Filed: Feb. 13, 2004

(65) Prior Publication Data

US 2004/0236165 A1 Nov. 25, 2004

Related U.S. Application Data

(63) Continuation of application No. 09/603,922, filed on Jun. 26, 2000, now abandoned.

(30) Foreign Application Priority Data

Jun. 24, 1999 (IT) ............................... MI99A1400
May 26, 2000 (IT) ........................... MI2000A1168

(51) Int. Cl.
 *C07C 5/00* (2006.01)
(52) U.S. Cl. ...................................... 585/418
(58) Field of Classification Search ................. 585/418
 See application file for complete search history.

(56) References Cited

U.S. PATENT DOCUMENTS

| 3,926,782 | A | 12/1975 | Plank et al. |
| 3,953,366 | A | 4/1976 | Morrison |
| 4,175,057 | A | 11/1979 | Davies et al. |
| 4,276,437 | A | 6/1981 | Chu |
| 4,441,991 | A | 4/1984 | Dwyer et al. |
| 4,485,185 | A | 11/1984 | Onodera et al. |
| 4,543,347 | A | 9/1985 | Heyward et al. |
| 4,629,818 | A | 12/1986 | Burress |
| 4,854,939 | A | 8/1989 | Harandi et al. |
| 4,855,522 | A | 8/1989 | Diaz |
| 4,861,933 | A | 8/1989 | Nemet-Mavrodin |
| 4,891,463 | A | 1/1990 | Chu |
| 5,026,938 | A | 6/1991 | Shum |
| 5,240,892 | A | 8/1993 | Klocke |
| 6,034,291 | A | 3/2000 | Girotti et al. |

FOREIGN PATENT DOCUMENTS

| EP | 0 130 251 | 1/1985 |
| EP | 0 151 351 | 8/1985 |
| EP | 0 309 089 | 3/1989 |
| EP | 0 378 916 | 7/1990 |

*Primary Examiner*—Thuan Dinh Dang
(74) *Attorney, Agent, or Firm*—Oblon, Spivak, McClelland, Maier & Neustadt, P.C.

(57) ABSTRACT

Aromatic hydrocarbon compounds are produced by a process of contacting one or more aliphatic hydrocarbons containing from 3 to 6 carbon atoms with a catalytic composition comprising (i) gallium, (ii) at least one lanthanide element, and (iii) a zeolite selected from the group consisting of the MIF family of zeolites, the crystal lattice of which consists of silicon oxide and aluminum oxide in a molar ratio of silicon oxide to aluminum oxide which is greater than 20 and less than 500, and is comprised of crystallites, at least 90% of which have diameters smaller than 500 Å.

22 Claims, 3 Drawing Sheets

CATALYTIC COMPOSITION FOR THE AROMATIZATION OF HYDROCARBONS

CROSS-REFERENCE TO RELATED APPLICATIONS

Figure 1:
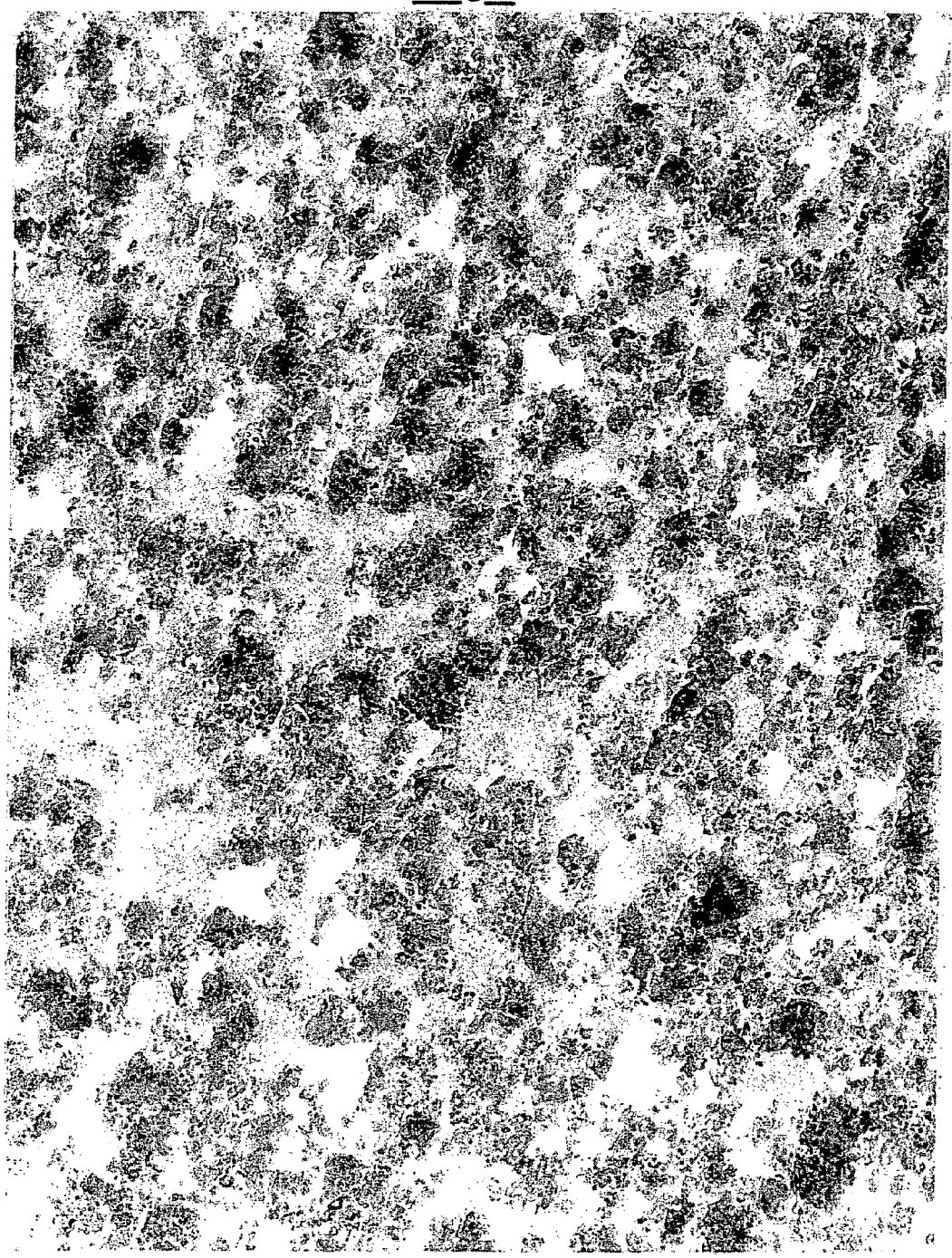

The present application is a continuation of application Ser. No. 09/603,922 filed Jun. 26, 2000, now abandoned.

BACKGROUND OF THE INVENTION

1. Field of the Invention

The present invention regards a catalytic composition comprising gallium, at least one element chosen in the group of the lanthanides, and a zeolite of MFI, MEL or MFI/MEL structure, the crystal lattice of which is made up of silicon oxide and at least one metal oxide chosen from among aluminium oxide, boron oxide and gallium oxide. Preferably, in the catalytic compositions of the present invention a zeolite is used belonging to the MFI family characterized by crystallites which for at least 90% have a diameter smaller than 500 Å and which can form agglomerates of submicron dimensions characterized by possessing at least 30% of the extrazeolitic porosity in the region of the mesopores.

In addition, the catalytic compositions of the present invention can contain rhenium.

These catalytic compositions are useful in processes of aromatization of aliphatic hydrocarbons having from 3 to 6 carbon atoms.

2. Description of the Background

The reaction of aromatization of paraffins and light olefins ($C_2$–$C_5$) to yield mixtures of benzene, toluene, ethylbenzene and xylenes (BTEX) has for many years been a subject of study. In 1973, the use was described of zeolites having an MFI structure (ZSM-5, ZSM-11, ZSM-21) for the aromatization of light hydrocarbons (both saturated and unsaturated) resulting from cracking, and from the production of coker gasoline or pyrolysis gasoline (U.S. Pat. No. 3,756,942 and U.S. Pat. No. 3,845,150).

U.S. Pat. No. 4,175,057 and U.S. Pat. No. 4,180,689 describe the reaction of aromatization of propane and butane in the presence of a catalyst with a base of gallium and an MFI zeolite. These patents were followed by numerous others regarding various modifications of this process involving modifications of the catalyst (U.S. Pat. No. 4,795,844), of the throughput (EP 252705, EP 050021 and U.S. Pat. No. 4,350,835) and of the system of introduction of gallium (EP 120018 and EP 184927). In particular, EP 252705 describes a process for producing aromatic compounds from feedstock containing $C_2$–$C_{12}$ aliphatic hydrocarbons, using a catalyst comprising a zeolite, having a constraint index from 1 to 12, a preferably very high silica/alumina ratio, and from 0.5 to 10% of gallium. Possibly, other elements chosen from among the metals belonging to the Groups I–VIII may be present.

It has moreover been found that the addition of platinum and palladium to the Ga and MFI zeolite-based catalyst determines an improvement in the aromatic-compound selectivity and reduces the formation of coke on the catalyst (U.S. Pat. No. 4,407,728 and EP 215579, 216491, 224162, 228267). The presence of these metals increases, however, the formation of methane and ethane deriving from cracking. Subsequently, it was found that the introduction of rhenium, in the presence of platinum or palladium, determines a further improvement in the aromatic-compound selectivity, but also in this case there is an increase in the amount of $C_1$–$C_2$ light paraffins among the products (U.S. Pat. No. 4,766,265). Catalytic compositions containing copper, or chromium, and an MFI zeolite determine the formation of smaller amounts of methane, but the aromatic-compound selectivity remains smaller than the one obtained with catalytic compositions containing gallium and an MFI zeolite (P. Meriaudeau et al., Zeolites: Facts, Figures, Future, 1423–1429, 1989; E. S. Shapiro et al., International Symposium on Zeolites as Catalysts, Sorbents and Detergent Builders, Wurzburg (RFA), p. 73, 1988).

Also described are catalysts containing an MFI zeolite, a noble metal of the Pt family, a metal chosen from among Sn, Ge, In and Pb, and an alkaline and/or alkaline earth component (EP 474536). This catalytic system involves an improvement in the aromatic-compound selectivity as compared to the foregoing materials.

All the catalytic systems described above are characterized by a very short life, since, an account of the high temperatures necessary for the reaction of aromatization of olefins and light paraffins, there is an important phenomenon of fouling and formation of coke inside the pores of the catalyst. This phenomenon is linked essentially to phenomena of cracking and/or of polycondensation of the compounds present in the reaction environment.

SUMMARY OF THE INVENTION

There has now been surprisingly found a catalytic system comprising gallium, at least one element chosen in the group of the lanthanides and a zeolite based on silica and at least one metal oxide chosen from among alumina, boron oxide and gallium oxide, belonging to the MFI, MEL or MFI/MEL families, which, in the reaction of aromatization of $C_3$–$C_6$ light hydrocarbons, enables higher levels of selectivity to be obtained as compared to known catalytic systems, in particular those based on gallium and MFI zeolite, and moreover presents a greater resistance to deactivation, with a consequent considerable increase in life.

DETAILED DESCRIPTION OF THE PREFERRED EMBODIMENTS

A first subject of the present invention is therefore a catalytic composition comprising gallium, at least one element chosen in the group of the lanthanides and a zeolite belonging to the MFI, MEL or MFI/MEL families, the crystal lattice of which is made up of silicon oxide and at least one metal oxide chosen from among aluminium oxide, boron oxide and gallium oxide. This catalytic composition can, in addition, contain rhenium, and hence a particular aspect of the present invention is a catalytic composition comprising rhenium, gallium, at least one element chosen in the group of the lanthanides and a zeolite belonging to the MFI, MEL or MFI/MEL families, the crystal lattice of which is made up of silicon oxide and at least one metal oxide chosen from among aluminium oxide, boron oxide and gallium oxide.

The zeolite of the MFI family which is particularly suited for being used in the present invention is the zeolite ZSM-5 having a crystal lattice based on silicon oxide and aluminium oxide, as described in U.S. Pat. No. 3,702,886. Other zeolites of the MFI family which are particularly suited for being used in the present invention are the zeolites having an MFI structure based on silicon oxide, gallium oxide, and possibly aluminium oxide, as described in EP 252705, as well as the zeolites having an MFI structure based on silicon oxide and boron oxide, as described in U.S. Pat. No. 4,656,016.

In the MEL family, the zeolite which is best suited for being used in the catalytic composition of the present invention is ZSM-11, described in U.S. Pat. No. 3,709,979. Other zeolites of the family MEL which are particularly suited for being used in the present invention are the zeolites having an MEL structure based on silicon oxide and boron oxide, as described in J. Appl. Cryst. (1984), 17, 403–410. In the MFI/MEL family, a zeolite that can well be used is ZSM-8, described in GB 1334243. Likewise usable is the zeolite having an MFI/MEL structure based on silicon oxide and boron oxide, as described in ACS Symp. Series 398, p. 361 (1989).

Forming a particularly preferred aspect of the present invention are the catalytic compositions containing the ZSM-5 zeolite.

Preferably, in the catalytic composition of the present invention the zeolite is partially in acid form, i.e., part of the cationic sites present in the zeolite is occupied by hydrogen ions.

The molar ratio in the crystal lattice of the zeolite between silicon oxide and metal oxide, where the metal oxide is chosen from among aluminium oxide, boron oxide and gallium oxide or their mixtures, is preferably greater than 20. A preferred aspect is that said ratio is greater than 20 and less than 500, preferably, greater than 20 and less than 400. An even more preferred aspect is that said ratio is greater than 20 and less than 200, preferably, greater than 20 and less than 100. A still more preferred aspect is that said ratio is greater than 20 and less than or equal to 70, preferably, greater than 20 and less than 60.

It has, in particular, been found that using, in the catalytic system of the present invention, an MFI zeolite characterized by an appropriate size of the crystallites, in the reaction of aromatization of $C_3$–$C_6$ light hydrocarbons, particularly high yields are obtained as compared to the known catalytic systems, with a greater percentage, in the fraction of the by-products, of recoverable products. Moreover, this catalytic system containing an MFI zeolite with sizes of the crystallites appropriately selected presents greater resistance to deactivation, with a consequent considerable increase in life.

A particular subject of the present invention is consequently a catalytic composition comprising gallium, at least one element chosen in the group of the lanthanides and a zeolite belonging to the MFI family characterized by crystallites which for at least 90% have diameters smaller than 500 Å. Preferably, the zeolite is partially in acid form.

Also this particular catalytic composition can, in addition, contain rhenium. The crystallites of the MFI zeolite used in this particular aspect of the present invention can present in the form of submicron mulberry-shaped aggregates with an extrazeolitic porosity of a meso-macroporous nature. By "extrazeolitic porosity" is meant the porosity obtained by summing the fraction of mesoporosity and macroporosity (determined by means of mercury-intrusion porosimetry up to a pressure of 2000 bar) present in the aggregate, hence excluding the contribution of the microporosity of the zeolite. The total volume of said extrazeolitic porosity is constituted for at least 30% by mesopores (diameter<500 Å). Preferably, in said catalytic compositions MFI zeolites are used consisting of crystallites with a diameter of less than 500 Å.

The zeolite of the MFI family having for at least 90% diameters of less than 500 Å which is very suitable for being used in this particular aspect of the invention is an MFI zeolite the crystal lattice of which is made up of silicon oxide and aluminium oxide (ZSM-5). A preferred aspect is that the molar ratio between the silicon oxide and aluminium oxide in the crystal lattice of said zeolite is greater than 20.

Preferably, said molar ratio is greater than 20 and less than 500, preferably, less than 400. An even more preferred aspect is that said ratio is greater than 20 and less than 200, preferably, greater than 20 and less than or equal to 100.

A process that can well be used for preparing this MFI zeolite having crystallites which for at least 90% have diameters smaller than 500 Å is described in U.S. Pat. No. 3,926,782. According to the method described in this patent, the MFI zeolites with crystallites of diameters for at least 90% smaller than 500 Å, usable in the catalytic compositions of the present invention, are prepared using a solution containing sources of tetra-propyl-ammonium ion, sodium oxide, aluminium oxide, silicon oxide, and water, having the following composition expressed as molar ratios:

$OH^-_{free}/SiO_2$:0.07–1.0
$(C_3H_7)_4N^+/SiO_2$:0.01–1
$H_2O/OH^-_{free}$:10–300
$SiO_2/Al_2O_3$:>5
$Na^+/SiO_2$:0.6–5 where by $OH^-_{free}$ are meant the $OH^-$ ions not neutralized by $H^+$ ions added to the reaction mixture directly, for example by means of acid compounds, or indirectly, for example using $Al(NO_3)_3$ or $Al_2(SO_4)_3$.

Preferably, the composition of the synthesis mixture is the following:

$OH^-_{free}/SiO_2$:0.1–0.3
$(C_3H_7)_4N^+/SiO_2$:0.05–0.25
$H_2O/OH^-_{free}$:20–60
$SiO_2/Al_2O_3$:50–120
$Na^+/SiO_2$:1–4

To obtain MFI zeolites having crystallites with diameters that for at least 90% are less than 500 Å, a high rate of stirring is required, and preferably the peripheral rate must be between 20 and 200 m/min. The conditions in which crystallization is conducted comprise a temperature in the range of from 90 to 130° C., under stirring for a time interval which ranges from 3 hours to 15 days, possibly followed by a second stage which can last up to 5 days in which the temperature is raised to a value ranging from 110 to 160° C. to accelerate completion of crystallization.

The source of tetra-propyl-ammonium ion can be the corresponding hydroxide or bromide, or tri-n-propylamine in a mixture with n-propyl bromide, dissolved in an appropriate solvent, such as methyl-ethyl-ketone.

The sources of silicon oxide comprise sodium silicate, silica hydrosol, silica gel and silicic acid. The source of aluminium oxide can be chosen from among sodium aluminate, alumina, aluminium salts, such as aluminium sulphate or aluminium nitrate.

The source of sodium can be chosen from among salts of sodium such as hydroxide, halides and/or sulphate. In addition or as an alternative, the sodium may be derived from the sources of aluminium and/or silicon which contain it.

To obtain the desired concentration of free $OH^-$ ions, mineral acid reagents, such as sulphuric acid or nitric acid can be added to the mixture.

The reagents can be mixed together in any order, crystallization is preferably conducted in autoclave.

In the catalytic compositions of the present invention, the element belonging to the group of the lanthanides that is preferably used is chosen from among neodymium and lanthanium, alone or in mixture with cerium and/or praseodymium. An even more preferred aspect is that the present invention uses mixtures of neodymium and lanthanium, possibly also containing cerium and/or praseodymium.

The lanthanide, or lanthanides, present in the catalytic composition according to the invention can be in the form of oxide, ion or metal, or can be present in a mixture of these forms. The amount of lanthanide, or lanthanides, expressed as element, can range from 0.01 to 10 wt %, preferably from 0.1 to 2 wt %, with respect to the total weight of the catalytic composition.

The gallium present in the catalytic composition can be in the form of oxide, gallium ion or metallic gallium, or can be a mixture of said forms. The amount of gallium, expressed as element, can range from 0.05 to 10 wt % with respect to the total weight of the catalytic composition, and is preferably from 0.5 to 4 wt %.

The gallium and the lanthanide can be introduced in the catalytic composition in any order, treating the zeolite, preferably in acid form, with a gallium compound and a lanthanide compound, or else, using a mixture containing both a gallium compound and a lanthanide compound, it is possible to introduce both the elements in the catalytic composition simultaneously.

When the catalytic composition of the present invention contains more than one lanthanide in its preparation, a mixture of compounds of these lanthanides will be used.

The best results in terms of catalytic activity are obtained when the catalytic composition is prepared by first introducing the gallium and then the lanthanide.

To introduce the gallium, any one of the known techniques can be used, such as mechanical mixing with gallium oxide, ion exchange or impregnation. Preferably, ion exchange or impregnation is used. In the first case, the zeolite is treated, preferably, in acid form, with an aqueous solution of a gallium salt having a concentration which can range from 0.01 to 0.5 M, for example a solution of gallium nitrate, gallium chloride or gallium sulphate, refluxed for 1–24 hours.

The specimen resulting from ion exchange, after appropriate washings with demineralized water, is dried at 100–150° C. and then calcined at a temperature ranging from 400 to 600° C. for 1–10 hours.

In the case where it is chosen to introduce the gallium using the impregnation technique, the zeolite is treated with the aqueous solution of a gallium salt, proceeding according to the known art of wet imbibition. This is followed by drying and calcining as in the case of ion exchange.

The stage of calcining determines at least partial transformation of the gallium ion into the corresponding oxide.

Ion exchange or impregnation are the techniques which are preferably used to introduce the gallium.

In the zeolite containing gallium, prepared in the foregoing stage with one of the techniques described above, the lanthanide can be introduced by means of the known techniques of mechanical mixing with an oxide of a lanthanide, impregnation or ion exchange. The techniques of ion exchange or impregnation are preferably used. In the former case, the composition containing the zeolite and the gallium is treated with an aqueous solution of a salt of the lanthanide, for example an aqueous solution of the corresponding nitrate, acetate, chloride or sulphate with a concentration of 0.01–0.5 M, refluxed for 1–24 hours. The specimen resulting from ion exchange, after appropriate washings, is dried and then calcined at a temperature ranging from 400 to 600° C. for 1–10 hours.

In the case where the lanthanide is introduced by impregnation, the procedure is according to the known art of wet imbibition. This is followed by drying and calcining as in the case of ion exchange.

On account of calcining, there will be an at least partial transformation of the lanthanide ion into the corresponding oxide.

Impregnation is the technique which is preferably used to introduce the lanthanide.

The two foregoing stages of introduction of the gallium and of the lanthanide can be carried out inverting the sequence and introducing the lanthanide before the gallium.

Whatever the sequence chosen, the calcining between the stage of introduction of the first metal and the stage of introduction of the second metal is optional; in the case where calcining was not carried out, the partial transformation of the metal ions into the corresponding oxides will take place simultaneously during calcining performed at the end of the second stage.

According to a particularly preferred aspect, the catalytic compositions of the present invention are prepared by depositing the gallium on the zeolite in acid form by means of ion exchange or impregnation, possibly calcining the product thus obtained, then depositing the lanthanide by impregnation and calcining the product obtained.

This may be followed by a stage of at least partial reduction of the lanthanide ion and of the gallium ion to the corresponding metals. The reduction to metal may be obtained by means of treatment of the catalytic composition with hydrogen or with a reducing agent, and can be performed on the catalytic composition before its use, or else in the reactor itself in which the catalytic composition will be used.

When the catalytic compositions of the present invention also contain rhenium, this can be in the form of oxide, ion or metal, or can be a mixture of said forms. The amount of rhenium, expressed as element, can range from 0.05 to 10 wt % with respect to the total weight of the catalytic composition, and preferably is from 0.5 to 4 wt %.

The rhenium can be introduced in any order into the catalytic composition with respect to the introduction of gallium and lanthanide, or else a mixture which contains all three elements can be used.

To introduce the rhenium any of the known techniques can be used, such as mechanical mixing with rhenium oxide, ion exchange or impregnation. Preferably, ion exchange or impregnation is used, performed with the techniques already previously described. Impregnation is the method which is preferably used, performed, for example, with an aqueous solution of rhenium chloride having a concentration of 0.01–0.5 M, applying the known art of wet imbibition. The product is then dried and calcined. During calcining, there is the at least partial transformation of the rhenium ion in the corresponding oxide.

A particularly preferred aspect is to introduce the rhenium into the catalytic composition after introducing the gallium and the lanthanide, i.e., treating the zeolite by means of ion exchange or impregnation with an aqueous solution of a gallium salt, drying, possibly calcining the resulting product, and then treating it by means of impregnation with an aqueous solution of lanthanide, drying it, possibly calcining it, and finally treating the resulting product with an aqueous solution of a rhenium salt, drying and calcining. A stage of reduction performed after introduction of the rhenium ion will result in the at least partial transformation of this ion into metallic rhenium.

The catalytic composition of the present invention can be used in mixture with appropriate binders, such as silica, alumina, and clay. The catalytic composition and the binder are mixed in a proportion ranging from 50:50 to 95:5, preferably from 60:40 to 90:10. The mixture of the two components is processed to obtain the desired final form, for example as cylindrical or spheroidal extrudate, or other known forms.

The catalytic compositions described above are useful in processes for the production of aromatic hydrocarbon compounds from light aliphatic hydrocarbons.

A further subject of the present invention is therefore a process for the production of aromatic hydrocarbon compounds, which comprises setting in contact one or more aliphatic hydrocarbons containing from 3 to 6 carbon atoms with a catalytic composition comprising gallium, at least one element chosen in the group of the lanthanides and a zeolite belonging to the MFI, MEL or MFI/MEL families, having a crystal lattice made up of silicon oxide and at least one oxide chosen from among aluminium oxide, boron oxide and gallium oxide.

A preferred aspect of the aromatization process according to the present invention uses a zeolite in the partially acid form. Among the zeolites that may be used, the zeolite ZSM-5 is preferred. The molar ratio in the crystal lattice of the zeolite between silicon oxide and metal oxide, where the metal oxide is chosen from among aluminium oxide, gallium oxide or their mixtures, is preferably greater than 20. A preferred aspect of the present invention is that said ratio is greater than 20 and smaller than 500, preferably smaller than 400. An even more preferred aspect is that said ratio is greater than 20 and less than 200, and still more preferably smaller than 100.

The best results are obtained when said ratio is greater than 20 and less than or equal to 70, preferably less than 60.

A particular aspect of the aromatization process of the present invention uses the catalytic compositions which additionally contain a rhenium ion, and hence a particular aspect of the present invention is a process for the production of aromatic hydrocarbon compounds which comprises setting in contact one or more aliphatic hydrocarbons containing from 3 to 6 carbon atoms with a catalytic composition comprising gallium, at least one element chosen in the group of the lanthanides and a zeolite belonging to the MFI, MEL or MFI/MEL families, having a crystal lattice made up of silicon oxide and at least one oxide chosen from among aluminium oxide, boron oxide and gallium oxide.

A further particular subject of the present invention is a process for the production of aromatic hydrocarbon compounds which comprises setting in contact one or more aliphatic hydrocarbons containing from 3 to 6 carbon atoms with a catalytic composition comprising gallium, at least one element chosen in the group of the lanthanides and a zeolite belonging to the MFI family characterized by crystallites which for at least 90% have diameters smaller than 500 Å. The zeolite is preferably in a partially acid form.

This catalytic composition can in addition contain rhenium.

Preferably, MFI zeolites are used consisting of crystallites having diameters of less than 500 Å. A particularly preferred aspect is to use MFI zeolites having for at least 90% diameters of less than 500 Å, the crystal lattice of which is made up of silicon oxide and aluminium oxide. Preferably, the molar ratio between silicon oxide and aluminium oxide in the crystal lattice of the said zeolite is greater than 20. A preferred aspect of the present invention is that said ratio is greater than 20 and smaller than 500, preferably smaller than 400. An even more preferred aspect is that said ratio is greater than 20 and less than 200, still more preferably, less than or equal to 100.

Preferred catalytic compositions are those containing neodymium or lanthanum, either alone or in mixture with cerium and/or praseodymium. An additional preferred aspect of the present invention is to use mixtures of neodymium and lanthanum, possibly also containing cerium and/or praseodymium.

In the aromatization process of the present invention, as aliphatic hydrocarbons containing from 3 to 6 carbon atoms, paraffins, olefins, cycloparaffins, cyclo-olefins or their mixtures may well be used. Preferably, aliphatic hydrocarbons containing from 4 to 5 carbon atoms are used.

Examples of aliphatic hydrocarbons that can well be used in the process of the present invention are n-pentane, n-pentenes, n-butane, n-butenes, iso-butane, iso-butene, methylbutenes, cyclopentenes, isopentane, cyclopentane, or their mixtures.

According to a preferred aspect of the invention, mixtures of hydrocarbons containing from 20 to 90 wt %, preferably from 40 to 70 wt %, of olefins, are used.

The aliphatic hydrocarbons having from 3 to 6 carbon atoms used in the process of the present invention can derive from steam cracking, FCC (fluid catalytic cracking) and thermal cracking, by means of the known methods of separation and distillation, and can contain smaller amounts of other types of hydrocarbons, such as aromatic hydrocarbons. They may also contain dienes (either linear or cyclic) in an amount not higher than 5 wt %. When this percentage of dienes is higher than 5 wt %, the charge of aliphatic hydrocarbons is subjected to a treatment of selective hydrogenation according to known methods, for example with a palladium-based catalyst, so as to bring the percentage of dienes to a value smaller than 5 wt %.

The process of the present invention is conducted at a temperature of between 300° and 800° C., preferably between 400° and 650° C., at a pressure of from 0 to 20 barg, preferably from 1 to 10 barg. The process is preferably conducted continuously, in a fixed-bed or fluidized-bed reactor, in the gas phase or partially liquid phase, at a weight hourly space velocity (WHSV, expressed as grams of feedstock/(grams of catalyst.hour)) ranging from 0.1 to 30 hours$^{-1}$, preferably from 0.5 to 10 hours$^{-1}$.

Hydrogen or inert gas (nitrogen) can be introduced in the reaction system as diluent.

Before the catalytic composition of the present invention is used, it was activated in nitrogen at a temperature ranging from 300 to 800° C., preferably from 300 to 700° C., for a period of between 1 and 24 hours, and at a pressure of between 0 and 10 barg.

In addition to or as a substitution for the foregoing procedure, activation with hydrogen can be performed at a temperature of 300–700° C., a pressure of 0–10 barg, for a period of between 1 and 24 hours.

EXAMPLE 1

Preparation of Ga-ZSM-5

25 g of a commercially available ZSM-5 zeolite (PQ Zeolites, CBV 3020), having a $SiO_2/Al_2O_3$ ratio of 30 and already exchanged into acid form, was treated with 470 ml of an aqueous solution of $Ga(NO_3)_3.9H_2O$ (0.02 M). Ion exchange was conducted under stirring and reflux for 2 hours. The catalyst was subsequently filtered, washed with distilled water, filtered again, and dried in air at 120° C.

Finally it was calcined in air at 550° C. for 5 hours. The final content of Ga was 2 wt %. The specimen is referred to as Ga-ZSM-5.

EXAMPLE 2

Preparation of GaNd (0.4)-ZSM-5

A catalyst having a final content of neodymium of 0.4 wt % was prepared starting from 8 g of the foregoing specimen of Example 1 (Ga-ZSM-5) by means of impregnation with 10 ml of an aqueous solution of $Nd(NO_3)_3 \cdot 6H_2O$ (0.020 M). The catalyst was subsequently dried at 120° C. and calcined in air at 550° C. for 5 hours. The specimen is referred to as GaNd (0.4)-ZSM-5.

EXAMPLE 3

Preparation of GaNd (1.0)-ZSM-5

The catalyst having a final content of neodymium of 1 wt % was prepared starting from 8 g of the Ga-ZSM-5 specimen of Example 1 by means of impregnation with 10 ml of an aqueous solution of $Nd(NO_3)_3 \cdot 6H_2O$ (0.045 M). The catalyst was subsequently dried at 120° C. and calcined in air at 550° C. for 5 hours. The specimen is referred to as GaNd (1.0)-ZSM-5.

EXAMPLE 4

Preparation of Ga(i)Nd (0.4)-ZSM-5

The catalyst Ga(i)Nd (0.4)-ZSM-5 (with a final content of Nd of 0.4 wt %) was prepared starting from 8 g of a commercially available ZSM-5 zeolite (PQ Zeolites, CBV 3020), having a $SiO_2/Al_2O_3$ ratio of 30 and already exchanged into acid form, by means of impregnation with an aqueous solution first of $Ga(NO_3)_3 \cdot 9H_2O$ (7.5 ml, 0.32 M), and then of $Nd(NO_3)_3 \cdot 6H_2O$ (10 ml, 0.020 M). Between the two impregnations, the catalyst was subjected to drying (in air at 120° C.). At the end of the operations, the specimen was subsequently dried at 120° C. and calcined in air at 550° C. for 5 hours. The specimen is referred to as Ga(i)Nd (0.4)-ZSM-5.

EXAMPLE 5

Preparation of Nd-ZSM-5

The Nd-ZSM-5 specimen was prepared by impregnation of 8 g of a commercially available ZSM-5 zeolite (PQ Zeolites, CBV 3020), having a $SiO_2/Al_2O_3$ ratio of 30 and already exchanged into acid form, by means of 10 ml of an aqueous solution of $Nd(NO_3)_3$ (0.020 M). The catalyst was subsequently dried at 120° C. and finally calcined in air at 550° C. for 5 hours. The final content of Nd was 0.4 wt %. The specimen is referred to as Nd-ZSM-5.

EXAMPLE 6

Aromatization Test of 1-pentene/n-pentane with HZSM-5 (Comparative)

An aromatization test of a charge of $C_5$ hydrocarbons (made up of 1-pentene and n-pentane in a weight ratio of 40:60) was conducted using an experimental apparatus consisting of a steel reactor (length=710 mm, internal diameter=12.5 mm, external diameter=35 mm) equipped with an internal thermometric sheath for control of the temperature. Heating took place with the aid of 4 ovens arranged in series along the reactor itself. The catalyst was introduced in the form of granules of appropriate sizes (20–40 mesh) and diluted with inert material. The feeding of the reagents (contained in a special refrigerated tank and kept under pressure in nitrogen) was performed using an HPLC pump. The products coming out of the reactor were condensed (at a temperature of 5° C.) and collected, partly in the liquid phase, and partly in the gas phase. Both the phases then underwent gas-chromatography analysis.

The catalyst used in this test was a commercially available ZSM-5 zeolite in acid form (commercial specimen PQ CBV 3020) having a $SiO_2/Al_2O_3$ ratio of 30.

The reaction conditions during the test were the following:

Reaction temperature: 350–400° C.
Pressure: 5 barg
WHSV: 5 g/g/hr
[1-pentene]/[n-pentane]: 40:60 w/w 3 g of catalyst were introduced in the reactor (the catalyst being obtained by tableting the powdered ZSM-5 zeolite at a pressure of 10 ton/cm², and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 1 gives the results of the test. In this table and in the tables of the ensuing examples of activity, the results are expressed in terms of conversion of the 1-pentene, value of the conversion of the n-pentane, final content by weight of BTEX product (benzene, toluene, ethylbenzene and xylene), of aromatic compounds (where $C_6$–$C_{10}$ benzene aromatic compounds are meant), of olefins (where all the olefins are meant, with the exclusion of non-reacted 1-pentene), of paraffins (where all the paraffins are meant, with the exclusion of non-reacted n-pentane) and of naphthalenes ($C_{10}$–$C_{13}$). Finally, the overall value of BTEX productivity is given (obtained from the start of the test up to value of time on stream of the corresponding sampling) calculated as:

BTEX productivity=kg BTEX producted/kg of catalyst

TABLE 1

| | | | |
|---|---|---|---|
| Time on stream (hours) | 4.5 | 7.5 | 17.5 |
| Temperature (° C.) | 400 | 350 | 350 |
| Conversion of 1-pentene (%) | 99.9 | 99.9 | 99.9 |
| Conversion of pentane (%) | 98.5 | 88.2 | 36.8 |
| BTEX (wt % over total) | 15.2 | 10.7 | 8.4 |
| Total aromatic compounds (wt %) | 18.4 | 15.9 | 13.4 |
| Total olefins (wt %) | 0.4 | 0.6 | 1.6 |
| Total paraffins (wt %) | 75.9 | 73.4 | 44.4 |
| Total naphthalenes (wt %) | 2.9 | 1.3 | 0.3 |
| BTEX productivity (kg/kg) | 2.9 | 4.2 | 8.2 |

EXAMPLE 7

Aromatization Test of 1-pentene/n-pentane with Ga-ZSM-5 (Comparative)

The aromatization test was conducted according to same procedure as indicated in Example 6.

The catalyst used in this test was the Ga-ZSM-5 zeolite prepared as indicated in Example 1.

The reaction conditions during the test were the following:

Reaction temperature: 400–500° C.
Pressure: 5 barg
WHSV: 10 g/g/hr
[1-pentene]/[n-pentane]: 40:60 w/w 2 g of catalyst were introduced in the reactor (the catalyst being obtained by tableting the powdered Ga-ZSM-5 zeolite of Example 1 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Table 2 gives the results of the test, expressed in a similar way as in Table 1.

TABLE 2

| Time on stream (hours) | 4.5 | 9.5 | 14.0 | 21.5 | 25.5 |
|---|---|---|---|---|---|
| Temperature (° C.) | 400 | 400 | 400 | 500 | 500 |
| Conversion of 1-pentene (%) | 99.9 | 99.9 | 99.9 | 99.9 | 98.6 |
| Conversion of pentane (%) | 97.6 | 87.9 | 52.2 | 57.0 | 0.0 |
| BTEX (wt % over total) | 16.8 | 14.2 | 11.8 | 14.6 | 3.3 |
| Total aromatic compounds (wt %) | 21.1 | 18.9 | 17.1 | 17.3 | 4.9 |
| Total olefins (wt %) | 0.4 | 1.3 | 2.6 | 9.4 | 19.2 |
| Total paraffins (wt %) | 75.3 | 70.7 | 49.4 | 43.5 | 10.3 |
| Total naphthalenes (wt %) | 0.7 | 0.3 | 0.4 | 2.76 | 0.3 |
| BTEX productivity (kg/kg) | 7.6 | 15.1 | 20.9 | 29.2 | 31.3 |

EXAMPLE 8 (Comparative)

Aromatization Test of 1-pentene/n-pentane with Nd-ZSM-5

The aromatization test was conducted according to same procedure as indicated in Example 6.

The catalyst used in this test was the Nd-ZSM-5 zeolite prepared as indicated in Example 5.

The reaction conditions during the test were the following:

Reaction temperature: 400–500° C.
Pressure: 5 barg
WHSV: 10 g/g/hr
[1-pentene]/[n-pentane]: 40:60 w/w 2 g of catalyst were introduced in the reactor (the catalyst being obtained by tableting the powdered Nd-ZSM-5 zeolite of Example 3 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Table 3 gives the results of the test, expressed in a similar way as in Table 1.

TABLE 3

| Time on stream (hours) | 5.5 | 9.0 | 17.2 |
|---|---|---|---|
| Temperature (° C.) | 400 | 400 | 500 |
| Conversion of 1-pentene (%) | 99.9 | 99.9 | 92.1 |
| Conversion of pentane (%) | 95.3 | 73.3 | 13.3 |
| BTEX (wt % over total) | 15.0 | 13.1 | 2.6 |
| Total aromatic compounds (wt %) | 19.0 | 18.8 | 3.4 |

TABLE 3-continued

| Total olefins (wt %) | 0.8 | 1.4 | 24.9 |
|---|---|---|---|
| Total paraffins (wt %) | 69.8 | 60.5 | 13.2 |
| Total naphthalenes (wt %) | 0.4 | 1.1 | 2.8 |
| BTEX productivity (kg/kg) | 7.5 | 12.8 | 18.0 |

In contrast to the foregoing comparative catalysts, the catalyst which contained neodymium alone revealed a loss of activity at 500° C., at lower time-on-steam values. The comparative catalyst that presented the best BTEX yields was the one containing gallium alone, whereas the catalyst containing neodymium alone had the worst yields, above all at 500° C., as well as a rapid decay.

EXAMPLE 9

Aromatization Test of 1-pentene/n-pentane with GaNd (0.4)-ZSM-5

The aromatization test was conducted according to same procedure as indicated in Example 6.

The catalyst used in this test was the GaNd(0.4)-ZSM-5 zeolite prepared as indicated in Example 2.

The reaction conditions during the test were the following:

Reaction temperature: 400–500° C.
Pressure: 5 barg
WHSV: 10 g/g/hr
[1-pentene]/[n-pentane]: 40:60 w/w 2 g of catalyst were introduced in the reactor (the catalyst being obtained by tableting the powdered GaNd(0.4)-ZSM-5 zeolite of Example 2 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Table 4 gives the results of the test, expressed in a similar way as in Table 1.

TABLE 4

| Time on stream (hours) | 5.5 | 9.0 | 17.2 | 31.2 | 36.2 |
|---|---|---|---|---|---|
| Temperature (° C.) | 400 | 400 | 400 | 500 | 500 |
| Conversion of 1-pentene (%) | 99.9 | 99.9 | 99.9 | 99.9 | 99.9 |
| Conversion of pentane (%) | 92.7 | 86.5 | 72.5 | 84.8 | 48.3 |
| BTEX (wt % over total) | 17.7 | 16.2 | 14.1 | 21.8 | 14.4 |
| Total aromatic compounds (wt %) | 22.8 | 21.5 | 18.8 | 25.1 | 17.6 |
| Total olefins (wt %) | 0.6 | 0.7 | 1.3 | 3.7 | 8.5 |
| Total paraffins (wt %) | 69.9 | 66.5 | 60.0 | 59.2 | 40.7 |
| Total naphthalenes (wt %) | 0.7 | 1.3 | 1.4 | 1.5 | 0.8 |
| BTEX productivity (kg/kg) | 8.7 | 14.1 | 25.2 | 40.7 | 48.4 |

As compared to the foregoing comparative catalysts, the catalyst of the present invention revealed better BTEX yield values both at 400° C. and at 500° C., as well as long performance life over time.

EXAMPLE 10

Aromatization Test of 1-pentene/n-pentane with GaNd (1.0)-ZSM-5

The aromatization test was conducted according to same procedure as indicated in Example 6.

The catalyst used in this test was the GaNd(1.0)-ZSM-5 zeolite prepared as indicated in Example 3.

The reaction conditions during the test were the following:

Reaction temperature: 400–500° C.
Pressure: 5 barg
WHSV: 10 g/g/hr
[1-pentene]/[n-pentane]: 40:60 w/w 2 g of catalyst were introduced in the reactor (the catalyst being obtained by tableting the powdered GaNd(1.0)-ZSM-5 zeolite of Example 3 at a pressure of 10 ton/cm², and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Table 5 gives the results of the test, expressed in a similar way as in Table 1.

TABLE 5

| Time on stream (hours) | 5.5 | 9.0 | 17.2 | 24.2 | 31.2 |
|---|---|---|---|---|---|
| Temperature (° C.) | 400 | 400 | 400 | 500 | 500 |
| Conversion of 1-pentene (%) | 99.9 | 99.9 | 99.9 | 99.9 | 99.9 |
| Conversion of pentane (%) | 92.8 | 87.6 | 46.9 | 88.2 | 36.0 |
| BTEX (wt % over total) | 15.4 | 16.9 | 11.0 | 23.2 | 15.2 |
| Total aromatic compounds (wt %) | 19.5 | 22.2 | 15.1 | 25.6 | 18.1 |
| Total olefins (wt %) | 2.2 | 1.0 | 1.6 | 2.5 | 5.0 |
| Total paraffins (wt %) | 68.9 | 65.9 | 49.0 | 62.0 | 35.2 |
| Total naphthalenes (wt %) | 1.3 | 1.5 | 0.7 | 1.3 | 1.1 |
| BTEX productivity (kg/kg) | 7.8 | 13.1 | 23.1 | 31.1 | 42.7 |

EXAMPLE 11

Aromatization Test of 1-pentene/n-pentane with GaNd (0.4)-ZSM-5

The aromatization test was conducted according to same procedure as indicated in Example 6.

The catalyst used in this test was the GaNd(0.4)-ZSM-5 zeolite prepared as indicated in Example 2.

The reaction conditions during the test were the following:

Reaction temperature: 350–475° C.
Pressure: 5 barg
WHSV: 1–2 g/g/hr
[1-pentene]/[n-pentane]: 40:60 w/w 3 g of catalyst were introduced in the reactor (the catalyst being obtained by tableting the powdered GaNd(0.4)-ZSM-5 zeolite of Example 2 at a pressure of 10 ton/cm², and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 6 gives the results of the test, expressed in a similar way as in Table 1.

TABLE 6

| Time on stream (hours) | 17.5 | 41.5 | 69.5 | 93.5 | 136.5 | 177.5 | 185 |
|---|---|---|---|---|---|---|---|
| WHSV (hours⁻¹) | 2 | 1 | 1 | 1 | 1 | 1 | 1 |
| Temperature (° C.) | 350 | 350 | 375 | 400 | 425 | 450 | 475 |
| Conversion of 1-pentene (%) | 99.9 | 99.9 | 99.9 | 99.9 | 99.9 | 99.9 | 99.9 |
| Conversion of pentane (%) | 85.4 | 72.0 | 81.4 | 90.7 | 91.5 | 88.0 | 75.3 |
| BTEX (wt % over total) | 13.1 | 16.5 | 20.5 | 21.8 | 28.9 | 25.6 | 24.6 |
| Total aromatic compounds (wt %) | 19.6 | 25.5 | 28.4 | 29.1 | 36.9 | 31.9 | 29.4 |
| Total olefins (wt %) | 0.7 | 1.2 | 1.2 | 1.1 | 1.4 | 2.6 | 3.3 |
| Total paraffins (weight %) | 68.1 | 47.9 | 54.6 | 57.4 | 48.2 | 53.3 | 48.9 |
| Total naphthalenes (weight %) | 0.4 | 3.3 | 1.2 | 2.6 | 3.9 | 1.8 | 1.2 |
| BTEX productivity (kg/kg) | 5.3 | 10.5 | 16.8 | 23.3 | 34.6 | 47.3 | 49.6 |

EXAMPLE 12

Aromatization Test of 1-pentene/n-pentane with GaNd (0.4)-ZSM-5 (1-pentene 60 wt %)

The aromatization test was conducted according to same procedure as indicated in Example 6.

The catalyst used in this test was the GaNd(0.4)-ZSM-5 zeolite prepared as indicated in Example 2.

The reaction conditions during the test were the following:

Reaction temperature: 350–475° C.
Pressure: 5 barg
WHSV: 1 g/g/hr
[1-pentene]/[n-pentane]: 60:40 w/w 3 g of catalyst were introduced in the reactor (the catalyst being obtained by tableting the powdered GaNd(0.4)-ZSM-5 zeolite of Example 2 at a pressure of 10 ton/cm², and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 7 gives the results of the test, expressed in a similar way as in Table 1.

TABLE 7

| Time on stream (hours) | 24.5 | 48.5 | 72.5 | 96.5 | 132.3 | 139.3 |
|---|---|---|---|---|---|---|
| WHSV (hours⁻¹) | 1 | 1 | 1 | 1 | 1 | 1 |
| Temperature (° C.) | 350 | 375 | 400 | 425 | 450 | 475 |
| Conversion of 1-pentene (%) | 99.9 | 99.9 | 99.9 | 99.9 | 99.9 | 99.9 |
| Conversion of pentane (%) | 81.3 | 93.4 | 93.1 | 97.2 | 94.5 | 90.0 |
| BTEX (wt % over total) | 21.8 | 30.1 | 27.2 | 39.7 | 29.8 | 25.8 |
| Total aromatic compounds (wt %) | 31.1 | 42.0 | 35.2 | 48.1 | 35.6 | 31.5 |
| Total olefins (wt %) | 1.4 | 0.6 | 0.9 | 0.7 | 1.7 | 2.3 |
| Total paraffins (wt %) | 51.0 | 47.0 | 53.5 | 41.4 | 54.6 | 53.8 |
| Total naphthalenes (wt %) | 3.8 | 2.2 | 4.0 | 4.6 | 2.7 | 5.5 |
| BTEX productivity (kg/kg) | 9.0 | 18.5 | 26.7 | 38.2 | 51.3 | 52.7 |

EXAMPLE 13

Preparation of GaLa(0.4)-ZSM-5

A catalyst having a lanthanum content of 0.4 wt % was prepared starting from 8 g of the foregoing specimen of Example 1 (Ga-ZSM-5) by means of impregnation with 12 ml of an aqueous solution of La(NO$_3$)$_3$.6H$_2$O (0.015 M). The catalyst was subsequently dried at 120° C. and calcined in air at 550° C. for 5 hours. The specimen is referred to as GaLa (0.4)-ZSM-5.

EXAMPLE 14

Aromatization Test of 1-pentene/n pentane with GaLa(0.4)-ZSM-5

The aromatization test was conducted according to same procedure as indicated in Example 6.

The catalyst used in this test was the GaLa(0.4)-ZSM-5 zeolite prepared as indicated in Example 13.

The reaction conditions during the test were the following:

Reaction temperature: 425–500° C.
Pressure: 5 barg
WHSV: 1 g/g/hr
[1-pentene]/[n-pentane]: 60:40 w/w 3 g of catalyst were introduced in the reactor (the catalyst being obtained by tableting the powdered GaLa(0.4)-ZSM-5 zeolite of Example 13 at a pressure of 10 ton/cm$^2$, and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 8 gives the results of the test, expressed in a similar way as in Table 1.

TABLE 8

| Time on stream (hours) | 24.5 | 48.5 | 72.5 | 96.5 |
|---|---|---|---|---|
| WHSV (hours$^{-1}$) | 1.25 | 1.25 | 1.25 | 1.25 |
| Temperature (° C.) | 425 | 450 | 475 | 500 |
| Conversion of 1-pentene (%) | 99.9 | 99.9 | 99.9 | 99.9 |
| Conversion of pentane (%) | 90.1 | 85.4 | 95.5 | 96.3 |
| BTEX (wt % over total) | 33.2 | 44.8 | 48.5 | 50.7 |
| Total aromatic compounds (wt %) | 39.7 | 52.5 | 54.0 | 54.8 |
| Total olefins (wt %) | 2.7 | 0.7 | 0.4 | 0.6 |
| Total paraffins (wt %) | 41.0 | 19.2 | 30.2 | 25.1 |
| Total naphthalenes (wt %) | 8.0 | 16.0 | 9.1 | 13.4 |
| BTEX productivity (kg/kg) | 13.8 | 26.6 | 40.8 | 55.8 |

EXAMPLE 15

Aromatization Test of 1-pentene/n-pentane with GaNd (0.4)-ZSM-5

The aromatization test was conducted according to same procedure as indicated in Example 6.

The catalyst used in this test was the GaNd(0.4)-ZSM-5 zeolite prepared as indicated in Example 2.

The reaction conditions during the test were the following:

Reaction temperature: 425–500° C.
Pressure: 5 barg
WHSV: 1 g/g/hr
[1-pentene]/[n-pentane]: 60:40 w/w 3 g of catalyst were introduced in the reactor (the catalyst being obtained by tableting the powdered GaNd(0.4)-ZSM-5 zeolite of Example 2 at a pressure of 10 ton/cm$^2$, and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 9 gives the results of the test conducted using the catalyst and the procedure specified in Example 15.

TABLE 9

| Time on stream (hours) | 24.5 | 72.5 | 96.5 | 102.5 |
|---|---|---|---|---|
| WHSV (hours$^{-1}$) | 1.25 | 1.25 | 1.25 | 1.25 |
| Temperature (° C.) | 425 | 450 | 475 | 500 |
| Conversion of 1-pentene (%) | 99.9 | 99.9 | 99.9 | 99.9 |
| Conversion of pentane (%) | 98.9 | 99.5 | 99.4 | 98.3 |
| BTEX (wt % over total) | 40.7 | 43.8 | 43.4 | 42.4 |
| Total aromatic compounds (wt %) | 47.2 | 49.4 | 48.0 | 46.4 |
| Total olefins (wt %) | 0.3 | 0.4 | 0.5 | 0.6 |
| Total paraffins (wt %) | 42.1 | 39.4 | 41.4 | 46.4 |
| Total naphthalenes (wt %) | 6.3 | 6.6 | 6.7 | 9.2 |
| BTEX productivity (kg/kg) | 10.8 | 37.8 | 51.1 | 54.3 |

EXAMPLE 16

Preparation of GaNd(0.4)Re-ZSM-5

A catalyst having a neodymium content of 0.4 wt % and a rhenium content of 0.5 wt % was prepared starting from 13 g of the foregoing specimen of Example 2 (GaNd(0.4)-ZSM-5) by means of impregnation with 15 ml of an aqueous solution of ReCl$_3$ (0.023 M). The catalyst was subsequently dried at 110° C. and calcined in air at 550° C. for 5 hours. The specimen is referred to as GaNd(0.4)Re-ZSM-5.

EXAMPLE 17

Aromatization Test of 1-pentene/n-pentane with GaNd(0.4)Re-ZSM-5

The aromatization test was conducted according to same procedure as indicated in Example 6.

The catalyst used in this test was the GaNd(0.4)Re-ZSM-5 zeolite prepared as indicated in Example 16.

The reaction conditions during the test were the following:

Reaction temperature: 425–500° C.
Pressure: 5 barg
WHSV: 1.25 g/g/hr
[1-pentene]/[n-pentane]: 60:40 w/w 3 g of catalyst were introduced in the reactor (the catalyst being obtained by tableting the powdered GaNd(0.4)Re-ZSM-5 zeolite of Example 16 at a pressure of 10 ton/cm$^2$, and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 10 gives the results of the test conducted using the catalyst and the procedure specified in Example 17.

TABLE 10

| Time on stream (h) | 24.5 | 72.5 | 114.0 | 138.0 |
|---|---|---|---|---|
| WHSV (hours$^{-1}$) | 1.25 | 1.25 | 1.25 | 1.25 |
| Tenperature (° C.) | 425 | 450 | 475 | 500 |
| Conversion of 1-pentene (%) | 99.9 | 99.9 | 99.9 | 99.9 |
| Conversion of pentane (%) | 96.4 | 99.0 | 95.7 | 96.3 |
| BTEX (wt % over total) | 46.7 | 47.7 | 47.7 | 49.1 |
| Total aromatic compounds (wt %) | 53.8 | 54.0 | 52.0 | 52.8 |
| Total olefins (wt %) | 0.4 | 0.2 | 0.6 | 1.1 |
| Total paraffins (wt %) | 31.0 | 32.5 | 35.0 | 35.1 |
| Total naphthalenes (wt %) | 8.4 | 8.0 | 6.6 | 5.5 |
| BTEX productivity (kg/kg) | 14.4 | 40.9 | 63.0 | 77.8 |

EXAMPLE 18

Preparation of GaTR(0.4)-ZSM-5

A catalyst having a rare-earth content of 0.4 wt % was prepared starting from 10 g of the foregoing specimen of Example 1 (Ga-ZSM-5) by means of impregnation with 15 ml of an aqueous solution containing 0.1 g of a mixture of carbonates of rare earths and 0.2 cc of $HNO_3$. The mixture of carbonates of rare earths comprised the following compounds: La (37.2 wt %), Nd (10.8 wt %) Ce (7.3 wt %), and Pr (4.5 wt %). The catalyst was subsequently dried at 110° C. and calcined in air at 550° C. for 5 hours. The specimen is referred to as GaTR(0.4)-ZSM-5.

EXAMPLE 19

Aromatization Test of 1-pentene/n-pentane with GaTR(0.4)-ZSM-5 (1-pentene 60 wt %)

The aromatization test was conducted according to same procedure as indicated in Example 6.

The catalyst used in this test was the GaTR(0.4)-ZSM-5 zeolite prepared as indicated in Example 18.

The reaction conditions during the test were the following:

Reaction temperature: 425–500° C.
Pressure: 5 barg
WHSV: 1.25 g/g/hr
[1-pentene]/[n-pentane]: 60:40 w/w 3 g of catalyst were introduced in the reactor (the catalyst being obtained by tableting the powdered GaTR(0.4)-ZSM-5 zeolite of Example 18 at a pressure of 10 ton/cm$^2$, and by grinding it and sifting it in granules having a size of 20–40 mesh) between two layers of inert material (corindone). The catalytic bed had a depth of 3–4 cm. Before the reaction, the material was activated in a current of nitrogen at 400° C. for 3–4 hours.

Table 11 gives the results of the test conducted using the catalyst and the procedure specified in Example 19.

TABLE 11

| | | | | |
|---|---|---|---|---|
| Time on stream (h) | 24.5 | 48.5 | 79.5 | 102.5 |
| WHSV (hours$^{-1}$) | 1.25 | 1.25 | 1.25 | 1.25 |
| Temperature (° C.) | 425 | 450 | 475 | 500 |
| Conversion of 1-pentene (%) | 99.9 | 99.9 | 99.9 | 99.9 |
| Conversion of pentane (%) | 98.3 | 97.6 | 94.3 | 95.6 |
| BTEX (wt % over total) | 39.0 | 41.0 | 42.0 | 43.8 |
| Total aromatic compounds (wt %) | 46.0 | 47.3 | 47.7 | 49.0 |
| Total olefins (wt %) | 0.5 | 0.4 | 1.1 | 1.3 |
| Total paraffins (wt %) | 36.2 | 36.9 | 37.0 | 36.6 |
| Total naphthalenes (wt %) | 10.3 | 10.1 | 8.0 | 7.7 |
| BTEX productivity (kg/kg) | 11.1 | 23.6 | 41.4 | 53.6 |

EXAMPLE 20

A solution A was prepared dissolving in succession 84.4 g of $Al_2(SO_4)_3.16 H_2O$, 327.6 g of tetrapropyl ammonium bromide, and 984.0 g of sodium chloride in 3096.0 g of water; next, 220.0 g of 96 wt % sulphuric acid were added. A solution B was prepared, made up of 2808 g of sodium silicate (27 wt % $SiO_2$, 8 wt % $Na_2O$) and 4480 g of water.

The solution B was introduced in a 20-litre autoclave, and the solution A was added under vigorous stirring. The final mixture obtained was crystallized at autogenous pressure, at a temperature of 100° C. for 10 days, stirring at a peripheral speed of 65 m/min.

After this period, the autoclave was cooled, the crystallization slurry was discharged, the solid phase was separated, washed by re-dispersion in water, and calcined at 550° C. for 5 hours. Next, the specimen was exchanged into acid form by treatment with ammonium acetate. The specimen thus obtained was characterized by a final $SiO_2/Al_2O_3$ molar ratio of 76.5.

At XRD analysis, the product was found to consist of pure MFI, characterized by the following cell parameters: a=20.1241(27)Å, b=19.9184(24)Å, c=13.4035(17)Å, V=5372.7(28) Å$^3$, mean size of the crystallites according to Scherrer's equation=280 Å in diameter. At TEM analysis, the zeolitic phase appeared in the form of relatively dense, mulberry-shaped submicron aggregates, which in turn consisted of regularly sized crystallites having diameters ranging from 200 to 500 Å. FIG. 1 presents a TEM micrograph of the specimen (enlargement 40000×). The specimen was characterized by means of mercury-intrusion porosimetry up to a pressure of 2000 bar: in the pressure range considered this analysis enables determination of the distribution of the pores with radiuses greater than 37 Å. The specimen was found to possess an extrazeolitic porosity of a substantially meso-macroporous nature, presenting 60.3% of the volume of the pores in the mesoporous region (diameter<500 Å). 90% of the porosity was between 37 and 1000 Å in radius, with a mean diameter of 480 Å.

EXAMPLE 21

20 g of zeolite obtained in foregoing example were impregnated with an aqueous solution first of $Ga(NO_3)_3.9H_2O$ (20 ml, 0.43 M) and subsequently of $Nd(NO_3)_3.6H_2O$ (20 ml, 0.023 M). Between the two impregnations the catalyst was subjected to drying (in air at 120° C.). At the end of the operations, the specimen was subsequently dried at 120° C. and calcined in air at 550° C. for 5 hours. The specimen thus obtained was characterized by a final $SiO_2/Al_2O_3$ molar ratio of 76.5, a final Ga content of 3.17 wt % and a final Nd content of 0.31 wt %.

EXAMPLE 22

Example 20 was repeated using 99.6 g of $Al_2(SO_4)_3.16H_2O$ and 213.3 g of $H_2SO_4$ (96 wt %). The final specimen exchanged into acid form was characterized by a $SiO_2/Al_2O_3$ molar ratio of 65.8. At XRD analysis the product was found to consist of pure MFI, characterized by the following cell parameters: a=20.1232(29) Å, b=19.9155(26) Å, c=13.40045(18) Å, V=5370.4(29) Å$^3$, mean size of the crystallites according to Scherrer's equation=245 Å in diameter. At TEM analysis, the zeolitic phase appeared in the form of relatively dense, mulberry-shaped submicron aggregates, which in turn consisted of regularly sized crystallites having diameters within the 200–500 Å range.

EXAMPLE 23

20 g of zeolite obtained according to the foregoing example were treated as described in Example 21, using an aqueous solution first of $Ga(NO_3)_3.9H_2O$ (40 ml, 0.22 M) and subsequently of $Nd(NO_3)_3.6H_2O$ (38 ml, 0.013 M). A catalyst was obtained with a final Ga content of 2.73 wt % and Nd content of 0.44 wt %.

EXAMPLE 24

Figure 2:
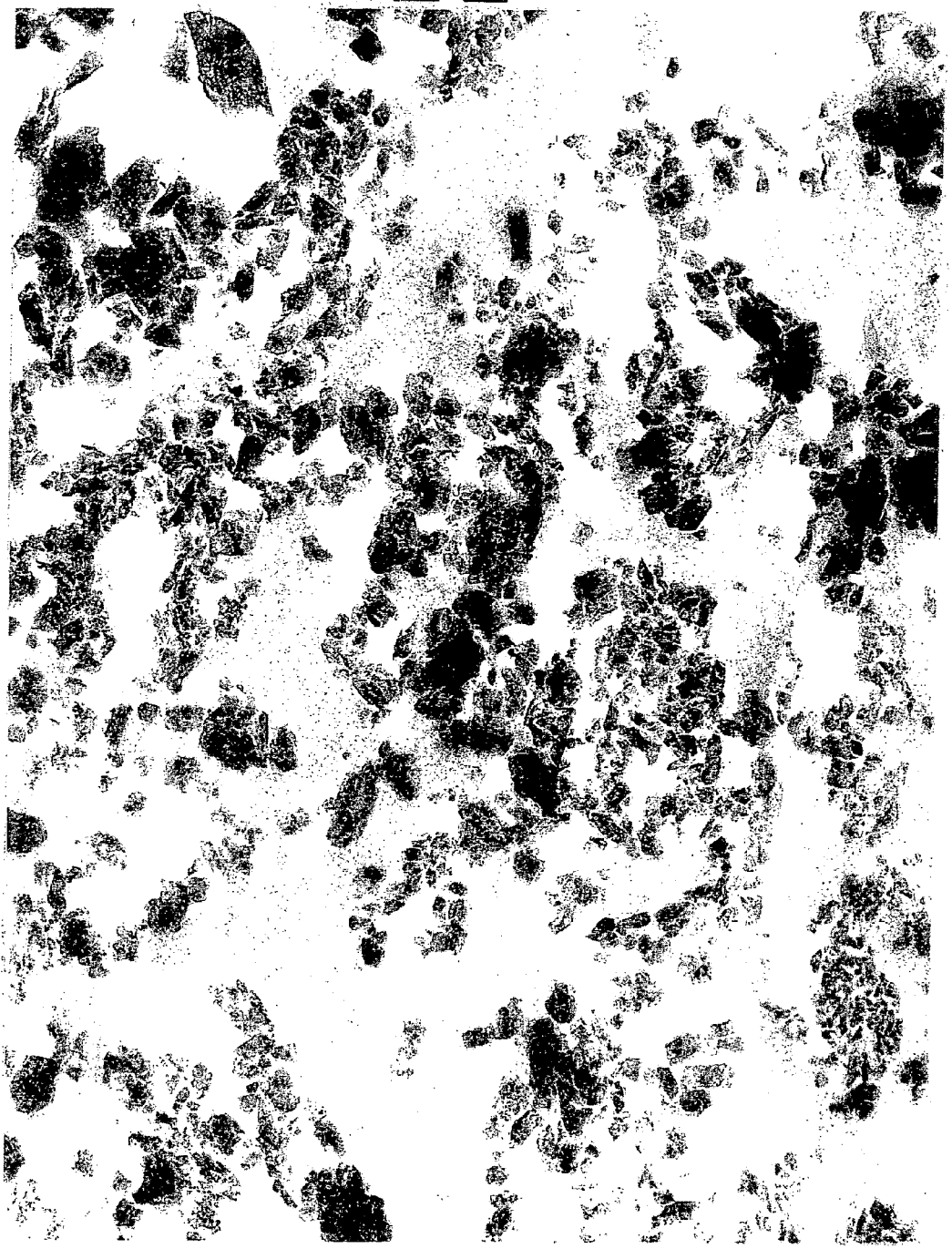

For this example, a commercially available ZSM-5 zeolite (PQ Zeolites, CBV 3020) was used, already exchanged into acid form, consisting of crystallites having a wide diameter distribution of between 100 and 1000 Å, and a mean diameter, estimated by means of Scherrer's equation, of 505 Å. A specimen of this zeolite was characterized by means of mercury-intrusion porosimetry up to a pressure of 2000 bar. The specimen was found to possess substantially an extrazeolitic porosity distributed in the macroporosity range, only 8.5% of the porous volume being included in the mesoporosity region (diameter<500 Å). The mean diameter of the pores was 1790 Å. FIG. 2 presents the TEM micrograph of the specimen (enlargement 40000×), in which a significant presence of crystallites of diameter greater than 500 Å may be noted, as well as a wider distribution of the diameters of the crystallites as compared to the specimen of Example 20 (FIG. 1).

20 g of the zeolite described above were impregnated with an aqueous solution first of $Ga(NO_3)_3 \cdot 9H_2O$ (20 ml, 0.43 M) and subsequently of $Nd(NO_3)_3 \cdot 6H_2O$ (20 ml, 0.023 M). Between the two impregnations, the catalyst was subjected to drying (in air at 120° C.). At the end of the operations, the specimen was subsequently dried at 120° C. and calcined in air at 550° C. for 5 hours. The resulting specimen was characterized by a final $SiO_2/Al_2O_3$ molar ratio of 32.1, a final Ga content of 2.96 wt %, and a final Nd content of 0.23 wt %.

EXAMPLE 25

Aromatization Test at Constant Temperature of 1-pentene/n-pentane

An aromatization test of a charge of $C_5$ hydrocarbons (made up of 1-pentene and n-pentane in a weight ratio of 60:40) was conducted using an experimental apparatus consisting of a steel reactor (length=710 mm, internal diameter=12.5 mm, external diameter=35 mm) equipped with an internal thermometric sheath for control of the temperature. Heating took place with the aid of 4 ovens arranged in series along the reactor itself. The catalyst was introduced in the form of granules of appropriate sizes (20–40 mesh) and diluted with inert material (corindone). The feeding of the reagents (contained in a special refrigerated tank and kept under pressure in nitrogen) was performed using an HPLC pump. The products coming out of the reactor were condensed (at a temperature of 5° C.) and collected, partly in the liquid phase, and partly in the gas phase. Both the phases then underwent gas-chromatography analysis.

The catalyst used in this test was the one prepared according to Example 21.

The reaction conditions during the test were the following:

Reaction temperature: 450° C.
Pressure: 5.7 barg
WHSV: 1.25 g/g/hr
[1-pentene]/[n-pentane]: 60:40 w/w 3.07 g of catalyst were introduced in the reactor (the catalyst being obtained by tableting the powdered catalytic composition of Example 21 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Figure 3:
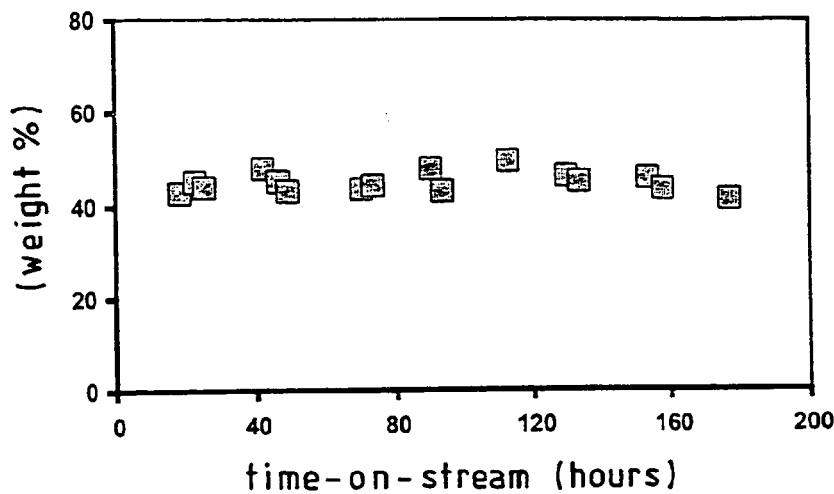

FIG. 3 gives the BTEX (benzene, toluene, ethylbenzene and xylene) yield values (wt % over total of the effluents of the reactor) that were obtained in the course of the test as the time on stream (t.o.s., hours) varied.

EXAMPLE 26

Aromatization Test at Constant Temperature of 1-pentene/n-pentane

The aromatization test was conducted according to the same procedure as the one indicated in Example 25.

The catalyst used in this test is the catalytic composition prepared according to Example 21.

The reaction conditions during the test were the following:

Reaction temperature: 500° C. (constant throughout the test)
Pressure: 5.7 barg
WHSV: 1.25 g/g/hr
[1-pentene]/[n-pentane]: 60:40 w/w 3.07 g of catalyst were introduced in the reactor (the catalyst being obtained by tableting the powdered catalytic composition of Example 21 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Figure 4:
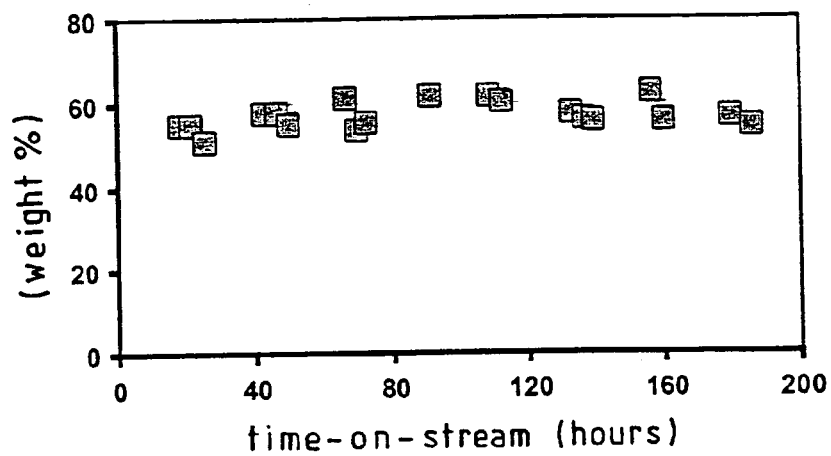

FIG. 4 gives the BTEX yield values (wt % over total of the effluents of the reactor) that were obtained in the course of the test as the time on stream (t.o.s., hours) varied.

EXAMPLE 27

Aromatization Test at Constant Temperature and High WHSV of 1-pentene/n-pentane The aromatization test was conducted according to the same procedure as the one indicated in Example 25.

In order to assess the performance of the catalyst in conditions of greater stress, the test was carried out at a WHSV value four times the value adopted in the foregoing examples.

The catalyst used in this test is the catalytic composition prepared according to Example 21.

The reaction conditions during the test were the following:

Reaction temperature: 500° C. (constant throughout the test)
Pressure: 5.7 barg
WHSV: 4 g/g/hr
[1-pentene]/[n-pentane]: 60:40 w/w 3.10 g of catalyst were introduced in the reactor (the catalyst being obtained by tableting the powdered catalytic composition of Example 21 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

Figure 5:
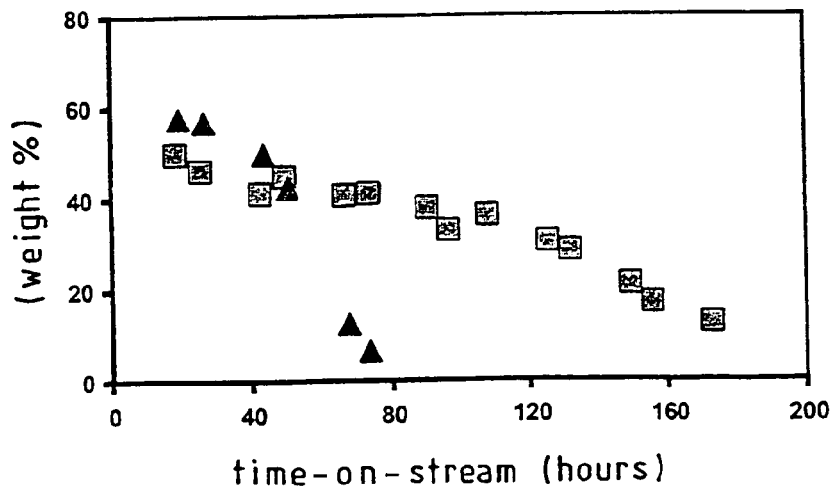

FIG. 5 gives the BTEX yield values (wt % over total of the effluents of the reactor) that were obtained in the course of the test as the time on stream (t.o.s., hours) varied. (Line ■).

EXAMPLE 28

Aromatization Test at Constant Temperature and High WHSV of 1-pentene/n-pentane The aromatization test was conducted according to the same procedure as the one indicated in Example 27.

The catalyst used in this test is the catalytic composition prepared according to Example 24.

The reaction conditions during the test were the following:

Reaction temperature: 500° C. (constant throughout the test)
Pressure: 5.7 barg
WHSV: 4 g/g/hr
[1-pentene]/[n-pentane]: 60:40 w/w 3.10 g of catalyst were introduced in the reactor (the catalyst being obtained by tableting the powdered catalytic composition of Example 24 at a pressure of 10 ton/cm$^2$, and by grinding it and sifting it in granules having a size of 20–40 mesh) between two layers of inert material (corindone). The catalytic bed had a depth of 2–3 cm. Before the reaction, the material was activated in a current of nitrogen at 400° C. for 3–4 hours.

FIG. 5 gives the BTEX yield values (wt % over total of the effluents of the reactor) that were obtained in the course of the test as the time on stream (t.o.s., hours) varied. (Line ▲).

An examination of the data of BTEX yield (wt % over total of the effluents of the reactor) given in FIG. 5, obtained from the aromatization tests conducted at T=500° C. and WHSV=4 h$^{-1}$ described in Examples 27 and 28, reveals how the catalytic performance of the catalyst of Example 21 and of the catalyst of Example 24 are similar for t.o.s. values smaller than 50 hours, whilst they differ for t.o.s. values greater than 50 hours.

EXAMPLE 29

Aromatization Tests at Variable Temperature of 1-pentene/n-pentane

With the purpose of maximizing the performance of the catalyst, it is a consolidated procedure to increase the temperature in the course of time. The ensuing Table 12 gives the data referring to two distinct tests, which were conducted according to the operating procedure described in Example 25, using the catalysts prepared according to Examples 23 and 24. In the course of these tests, the temperature T (expressed in ° C.) was increased at the end of time intervals Δt (in hours) set in an identical manner for each of the two catalysts.

Note that for equal t.o.s. values, at all the reaction temperatures considered the catalyst of Example 23 presents higher BTEXT yield values, as compared with the catalyst of Example 24.

TABLE 12

| | | Catalyst | |
|---|---|---|---|
| | | Example 24 BTEX yield | Example 23 BTEX yield |
| Δt [hours] | T [° C.] | (wt % over total) | (wt % over total) |
| 0–50 | 425 | 48 | 52 |
| 50–80 | 450 | 49 | 56 |
| 80–100 | 475 | 48.5 | 58 |

TABLE 12-continued

| | | Catalyst | |
|---|---|---|---|
| | | Example 24 BTEX yield | Example 23 BTEX yield |
| Δt [hours] | T [° C.] | (wt % over total) | (wt % over total) |
| 100–140 | 500 | 45 | 59 |
| 140–160 | 525 | 21 | 60 |
| 160–180 | 550 | — | 59 |
| 180–200 | 575 | — | 35 |

The invention claimed is:

1. A process for the production of aromatic hydrocarbon compounds, which comprises:
contacting one or more aliphatic hydrocarbons containing from 3 to 6 carbon atoms with a catalytic composition comprising (i) gallium, (ii) at least one lanthanide element, and (iii) a zeolite selected from the group consisting of the MFI family of zeolites, the crystal lattice of which consists of silicon oxide and aluminum oxide in a molar ratio of silicon oxide to aluminum oxide which is greater than 20 and less than 500, and is comprised of crystallites, at least 90% of which have diameters smaller than 500 Å to convert said aliphatic hydrocarbons to aromatic hydrocarbon compounds.

2. A process according to claim 1, in which the zeolite is ZSM-5.

3. A process according to claim 1, in which the ratio between silicon oxide and aluminum oxide is greater than 20 and less than or equal to 70.

4. A process according to claim 3, in which the ratio of silicon oxide to aluminum oxide is greater than 20 and less than 60.

5. A process according to claim 1, in which the MFI zeolite consists of crystallites with diameters smaller than 500 Å.

6. A process according to claim 1, in which the crystallites of the MIFI zeolite present in the form of mulberry-shaped submicron aggregates with an extrazeolitic porosity of a meso-macroporous nature.

7. A process according to claim 6, in which the total volume of said extrazeolitic porosity consists for at least 30% of pores with diameters of less than •Å.

8. A process according to claim 1, in which the molar ratio between silicon oxide and aluminum oxide is greater than 20 and less than or equal to 100.

9. A process according to claim 1, in which the zeolite is partially in acid form.

10. A process according to claim 1, in which the catalytic composition in addition contains rhenium.

11. A process according to claim 1 or claim 10, in which the lanthanide is selected from the group consisting of neodymium and lanthanum, either alone or in admixture with cerium and/or praseodymium, and mixtures of neodymium and lanthanum, optionally containing cerium and/or praseodymium.

12. A process according to claim 1 or claim 10, wherein said one or more aliphatic hydrocarbons containing from 3 to 6 carbon atoms are selected from the group consisting of olefins, cyclo-olefins, paraffins, and cycloparaffins.

13. A process according to claim 1 or claim 10, wherein the hydrocarbon or the aliphatic hydrocarbons contain from 4 to 5 carbon atoms.

14. A process according to claim 12, in which the aliphatic hydrocarbon is selected from the group consisting of n-pentane, n-pentenes, n-butane, n-butenes, iso-butane, iso-butene, methylbutenes, cyclopentenes, isopentane, cyclopentane, or their mixtures.

15. A process according to claim 1 or claim 10, in which mixtures of aliphatic hydrocarbons are used containing from 20 to 90 wt % of olefins.

16. A process according to claim 15, wherein mixtures of aliphatic hydrocarbons are used containing from 40 to 70 wt % of olefins.

17. A process according to claim 1 or claim 10, which is conducted at a temperature ranging from 300° to 800° C., and at a pressure ranging from 0 to 20 barg.

18. A process according to claim 17, which is conducted at a temperature ranging from 400° to 650° C., and at a pressure ranging from 1 to 10 barg.

19. A process according to claim 17, which is conducted at a WHSV ranging from 0.1 to 30 hours$^{-1}$.

20. A process according to claim 1, wherein said lanthanide element is present in the catalyst in an amount of 0.01 to 10 wt %, based on the total weight of the catalyst composition.

21. A process according to claim 1, wherein said gallium is present in the catalyst in an amount of 0.05 to 10 wt %, based on the total weight of the catalyst composition.

22. A process for the production of aromatic hydrocarbon compounds, which comprises:

contacting one or more aliphatic hydrocarbons containing from 3 to 6 carbon atoms with a catalytic composition comprising (i) gallium, (ii) at least one lanthanide element, and (iii) a zeolite selected from the group consisting of the MIFI family of zeolites, the crystal lattice of which consists of silicon oxide and aluminum oxide in a molar ratio of silicon oxide to aluminum oxide which is greater than 20 and less than 500, and is comprised of crystallites, at least 90% of which have diameters smaller than 500 Å, and wherein, in the process of introducing the zeolite with gallium and said at least one lanthanide, the process consists of introducing gallium and lanthanide elements into the zeolite and then drying and calcining the zeiolite product obtained.

* * * * *